(12) United States Patent
Hildebrandt et al.

(10) Patent No.: US 7,373,804 B1
(45) Date of Patent: May 20, 2008

(54) SCANNING BROOKFIELD DRY BLOCK

(75) Inventors: Marc J. Hildebrandt, Midland, MI (US); Theodore W. Selby, Midland, MI (US)

(73) Assignee: King Refrigeration, Inc., Freeland, MI (US)

( * ) Notice: Subject to any disclaimer, the term of this patent is extended or adjusted under 35 U.S.C. 154(b) by 520 days.

(21) Appl. No.: 10/929,828

(22) Filed: Aug. 30, 2004

(51) Int. Cl.
    *G01N 11/14* (2006.01)
(52) U.S. Cl. .................... 73/54.43; 73/54.28
(58) Field of Classification Search ........... 73/54.23, 73/54.28, 54.43
    See application file for complete search history.

(56) References Cited

U.S. PATENT DOCUMENTS

| 5,167,275 A | 12/1992 | Stokes et al. | |
| 5,503,002 A | 4/1996 | Selby et al. | 73/54.28 |
| 6,306,658 B1 | 10/2001 | Turner et al. | |
| 6,755,044 B1 | 6/2004 | Hildebrandt | 62/276 |
| 6,786,081 B1 | 9/2004 | Hildebrandt et al. | 73/54.43 |

OTHER PUBLICATIONS

Hildebrandt et al., U.S. Appl. No. 10/077,236, filed Feb. 15, 2002 A.D.
Hildebrandt et al., U.S. Appl. No. 10/674,168, filed Sep. 29, 2003 A.D.

*Primary Examiner*—Daniel S Larkin
(74) *Attorney, Agent, or Firm*—Christopher John Rudy (57) ABSTRACT

Scanning Brookfield dry block instrument component, viscometer instrument, and method of use of the instrument can employ direct refrigeration with heat provision. A thermoelectric chip substitute may be employed as well.

20 Claims, 7 Drawing Sheets

SCANNING BROOKFIELD DRY BLOCK

FIELD

This concerns a Scanning Brookfield Test (SBT) instrument component, viscometer, and method, in which control of temperature is carried out in a dry block, i.e., test cell temperature is not controlled with a liquid bath. Direct refrigeration with heat provision can be employed.

BACKGROUND

SBT instruments typically employ a liquid bath such as methanol to control temperature of test cell(s). See, e.g., U.S. Pat. No. 5,503,002 (Apr. 2, 1996) for a sensitive rotating viscometer instrument. Methanol, although a standard in the industry, has its well known drawbacks. Controlling the temperature and increasing efficiency are notable among concerns.

In addressing such drawbacks and concerns, and so forth, in various arts, new apparatuses were invented. Compare, U.S. Pat. No. 6,755,044 (Jun. 29, 2004) for a heater evaporator, and U.S. patent application Ser. Nos. 10/077,236 filed Feb. 15, 2002, which issued as U.S. Pat. No. 6,786,081 (Sep. 7, 2004), for direct and/or opposing flow path refrigeration, and 10/674,168 filed Sep. 23, 2003 for a directly refrigerated block.

It would be desirable to improve the SBT art.

DISCLOSURE

In addressing the desires, lacks and needs in the art, the present invention provides a scanning Brookfield dry block instrument component unit, viscometer instrument, and method of use of the instrument. Direct refrigeration with heat provision can be employed in the dry block.

The invention is useful in SBT methodology, especially in viscosity determination.

Significantly, by the invention, the SBT art is improved in kind. A most highly efficient test cell block arrangement is provided, in which temperature can be controlled to an outstanding degree, even as a dynamic system with scanning of the temperature, and the use and dangers of methanol are avoided. Numerous further advantages attend the invention.

The aforementioned patents, U.S. Pat. No. 5,503,002 and U.S. Pat. No. 6,755,044, and patent applications, U.S. Ser. No. 10/077,236 and U.S. Ser. No. 10/674,168, are incorporated herein by reference in their entireties.

The appended drawings form part of the present specification. With respect to the drawings, which depict certain illustrative embodiments of the invention, and which are not necessarily drawn to scale, and in which dimensions may be given, for an example, in inches, and may be considered to be approximate, the following is noted.

The invention can be further understood by the present detail, including that set forth below, which may be read in view of the drawings. The same is to be taken in an illustrative and not necessarily limiting sense.

Figures 1, 1A, 1B, 2:
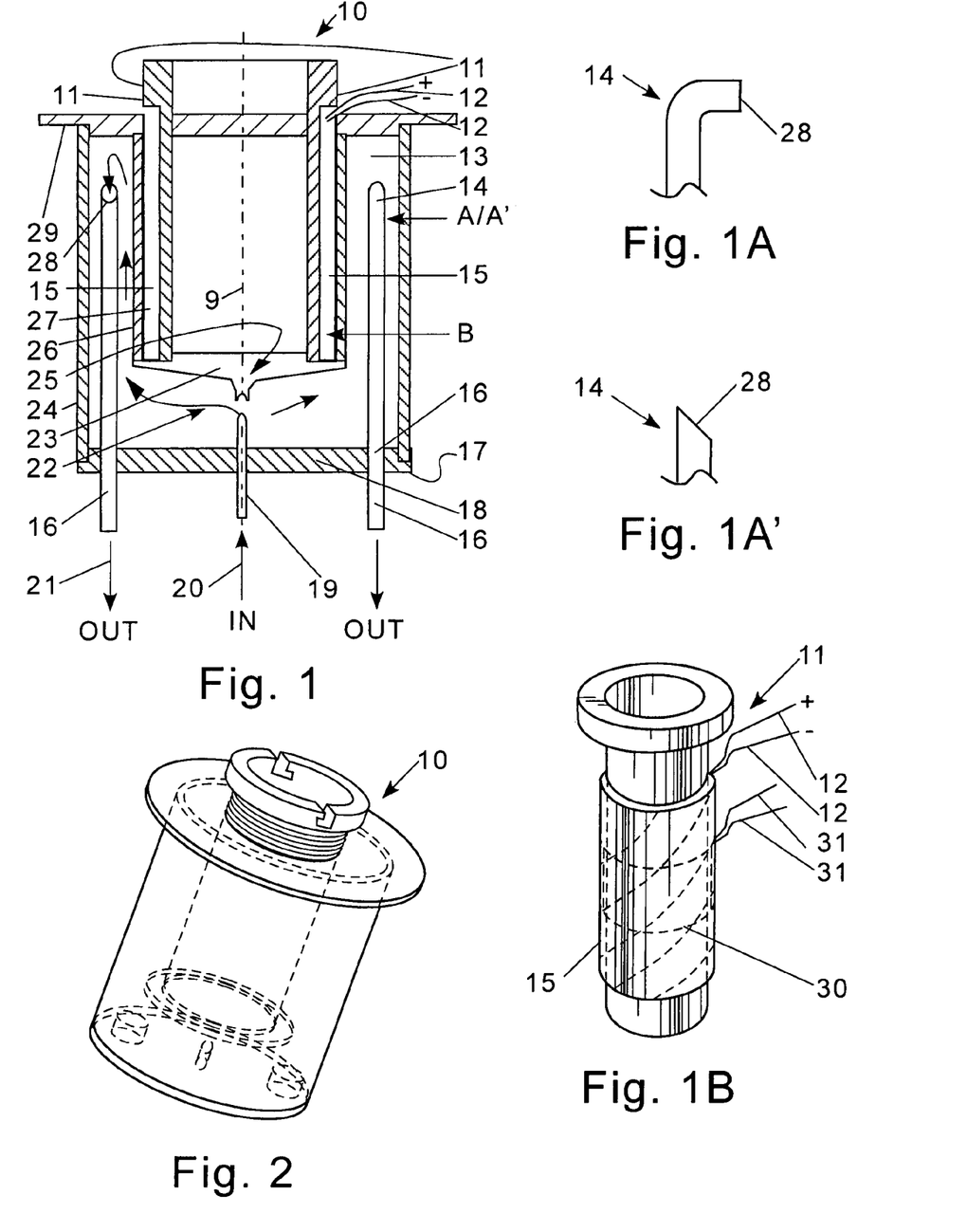
FIG. 1 is a side plan view in partial cross-section of a scanning Brookfield dry block evaporator-containing component of the invention.
FIGS. 1A and 1A' each show a view of a suction line inlet located at the top of a suction line, as taken along the arrow "A/A'" in FIG. 1, with the inlet of FIG. 1A' preferred.
FIG. 1B shows a view of a removable inner sleeve having a ribbon heater with an integral thermocouple (TC), as taken alone the arrow "B" in FIG. 1.
FIG. 2 is a perspective plan view of most of the component of FIG. 1.
Figure 3:
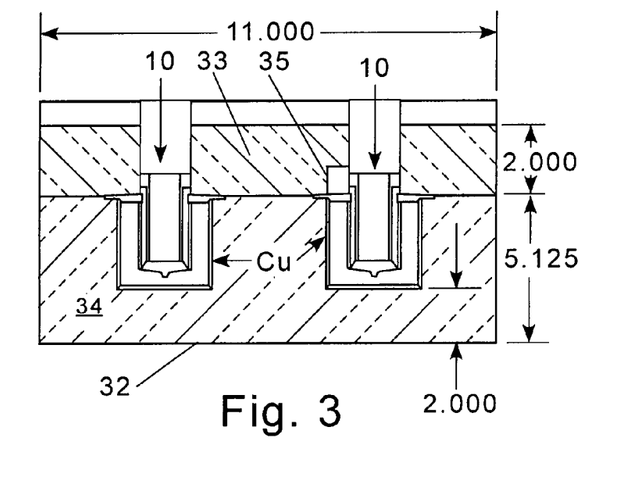
FIG. 3 is a front plan view of a dual block configuration, with two components of FIG. 1.
Figure 4:
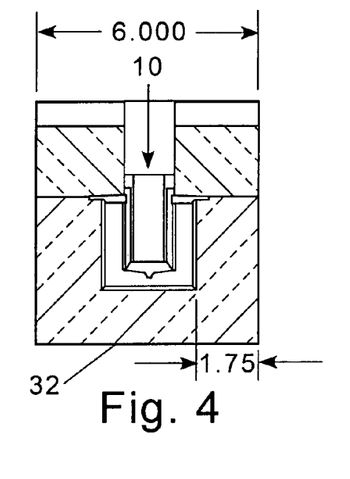
FIG. 4 is a side plan view of the configuration of FIG. 3.
Figure 5:
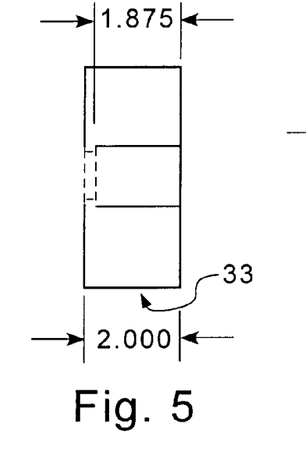
FIG. 5 is a side plan view of an upper insulation layer in the configuration of FIG. 3.
Figure 6:
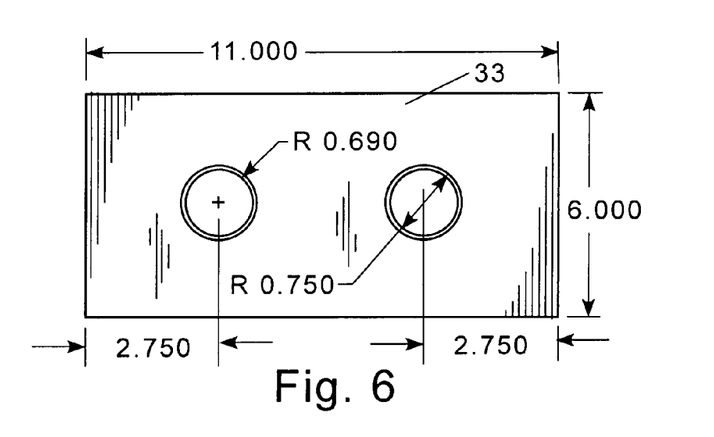
FIG. 6 is a top plan view of the insulation layer of FIG. 5.
Figure 7:
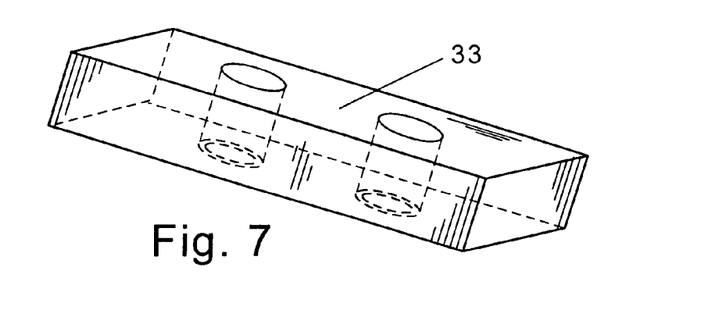
FIG. 7 is a perspective plan view of the insulation layer of FIG. 5.
Figure 8:
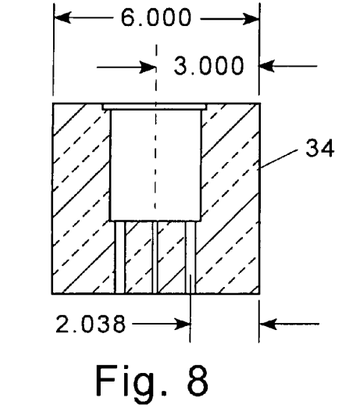
FIG. 8 is a side plan view of a lower insulation layer in the configuration of FIG. 3.
Figure 9:
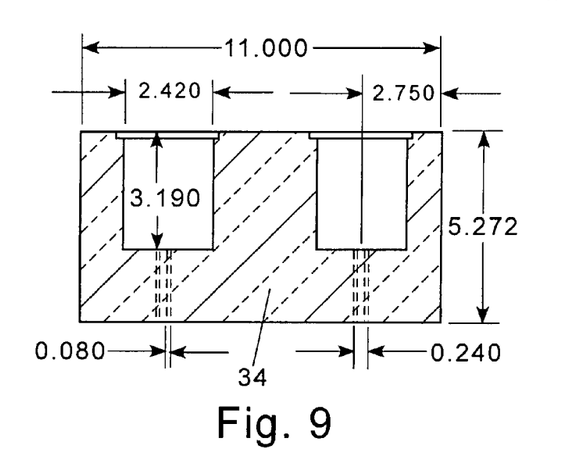
FIG. 9 is a front plan view of the insulation layer of FIG. 8.
Figure 10:
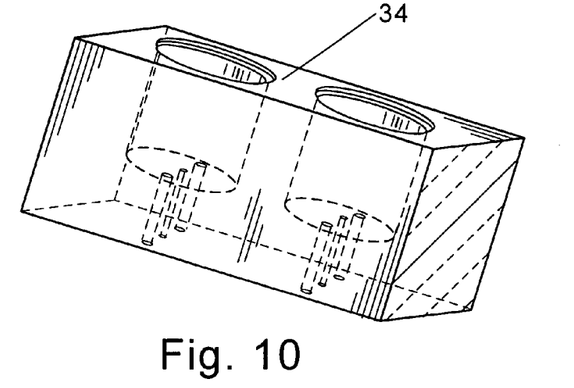
FIG. 10 is a perspective plan view of the insulation layer of FIG. 8.
Figure 11:
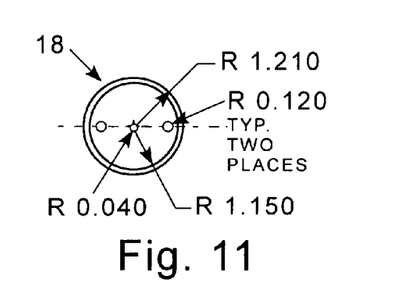
FIG. 11 is a top plan view of an evaporator bottom in the component of FIG. 1.
Figure 12:
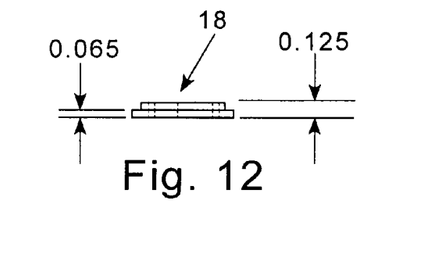
FIG. 12 is a side plan view of the bottom of FIG. 11.
Figure 13:
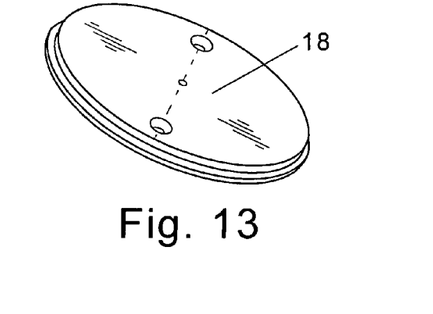
FIG. 13 is a perspective plan view of the bottom of FIG. 11.
Figure 14:
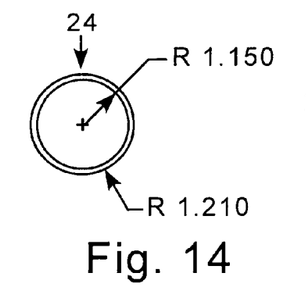
FIG. 14 is a top plan view of an outside evaporator sleeve in the component of FIG. 1.
Figure 15:
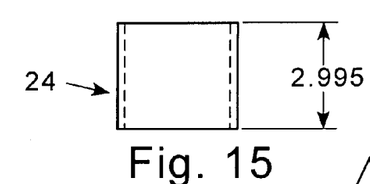
FIG. 15 is a side plan view of the sleeve of FIG. 14.
Figure 16:
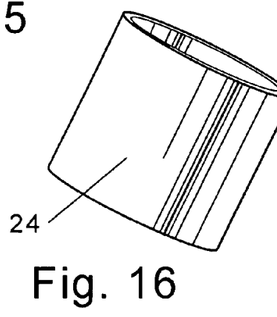
FIG. 16 is a perspective plan view of the sleeve of FIG. 14.
Figure 17:
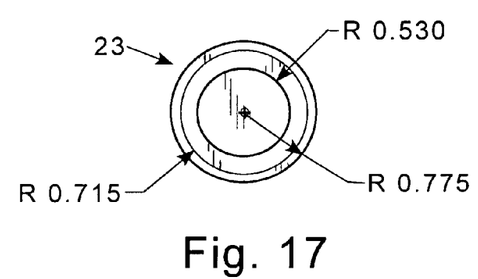
FIG. 17 is a top plan view of an evaporator inner bottom in the component of FIG. 1.
Figure 18:
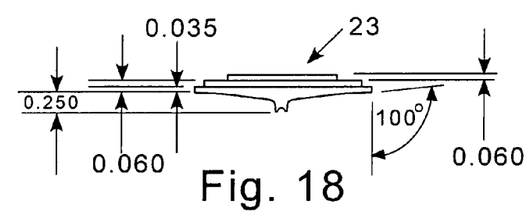
FIG. 18 is a side plan view of the bottom of FIG. 17.
Figure 19:
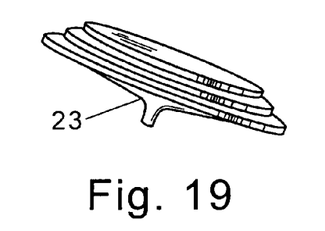
FIG. 19 is a perspective plan view of the bottom of FIG. 17.
Figure 20:
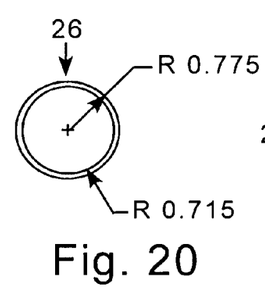
FIG. 20 is a top plan view of an inside evaporator sleeve in the component of FIG. 1.
Figure 21:
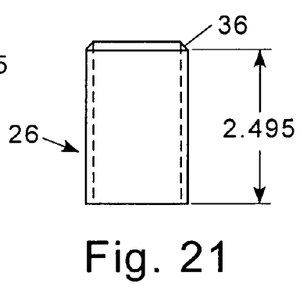
FIG. 21 is a side plan view of the sleeve of FIG. 20.
Figure 22:
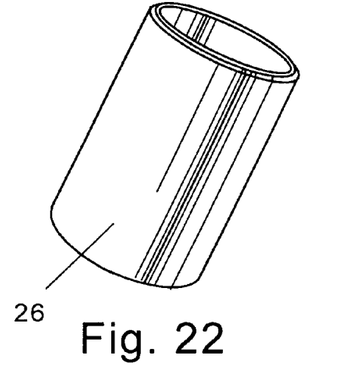
FIG. 22 is a perspective plan view of the sleeve of FIG. 20.
Figures 23, 24, 25, 26, 27, 28, 29:
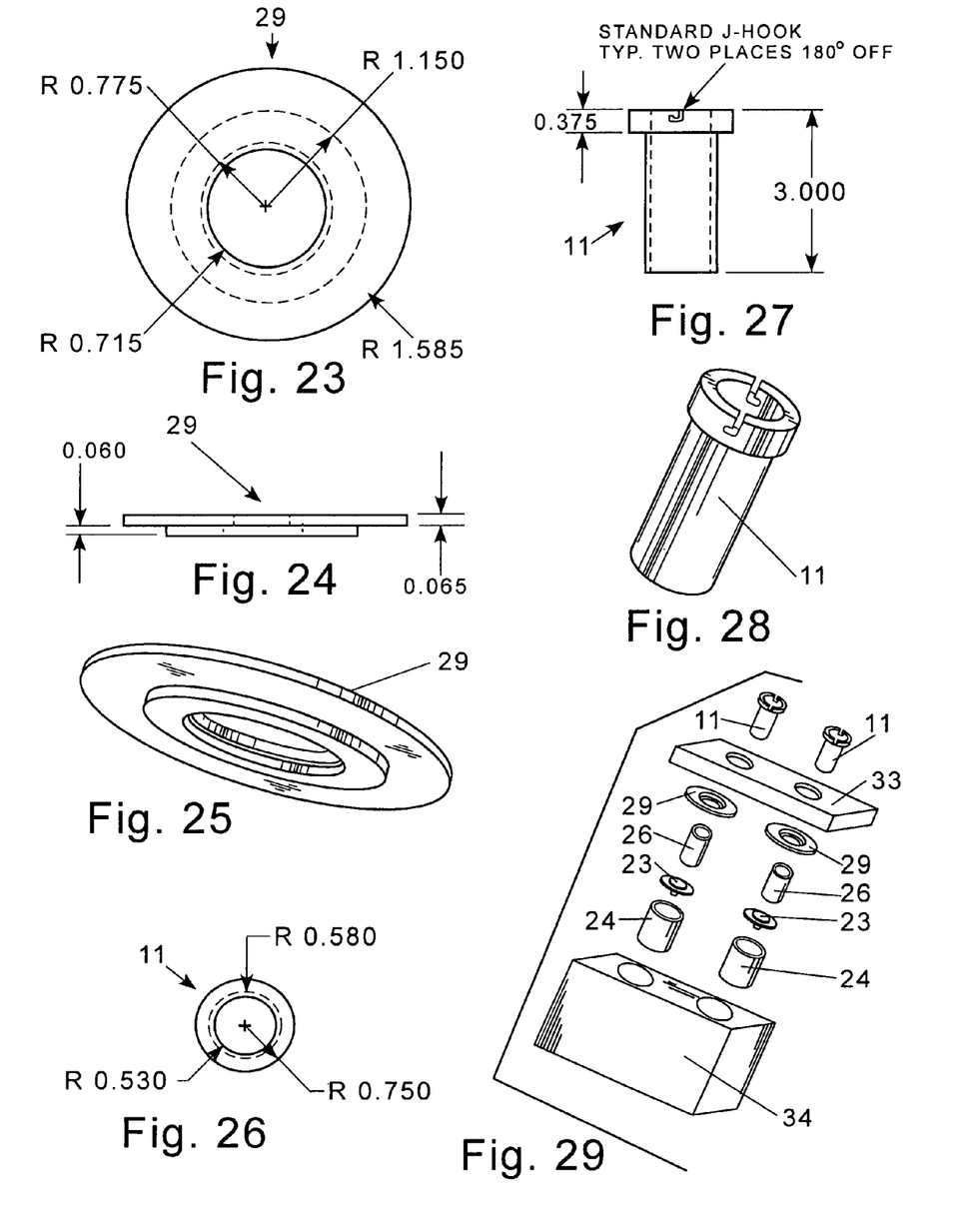
FIG. 23 is a top plan view of an evaporator top in the component of FIG. 1.
FIG. 24 is a side plan view of the top of FIG. 23.
FIG. 25 is a perspective plan view of the top of FIG. 23.
FIG. 26 is a top plan view of a test port sleeve in the component of FIG. 1.
FIG. 27 is a side plan view of the sleeve of FIG. 26.
FIG. 28 is a perspective plan view of the sleeve of FIG. 26.
FIG. 29 is an exploded perspective plan view of the configuration of FIG. 3.
Figure 30:
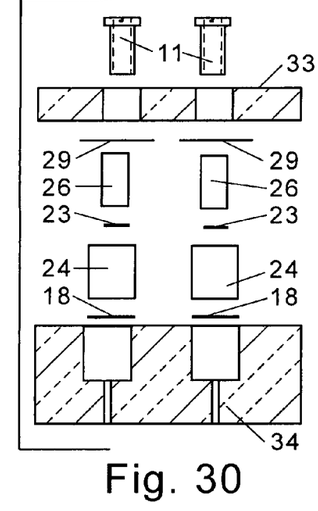
FIG. 30 is an exploded side plan view of the configuration of FIG. 3.
Figure 31:
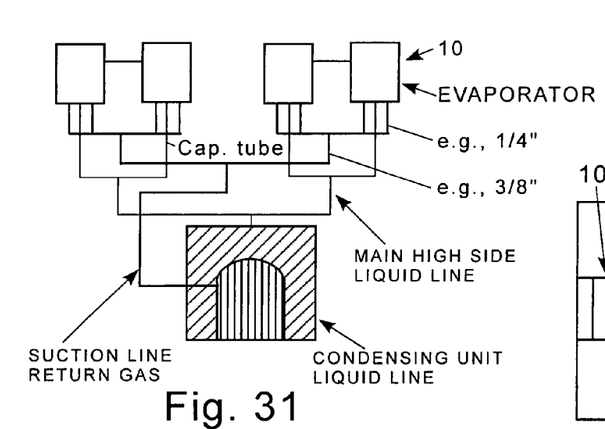
FIG. 31 is a plan view of a layout for four components of FIG. 1 or two configurations of FIG. 3 for an SBT rotating viscometer dry block apparatus having multiple test stations.
Figure 32:
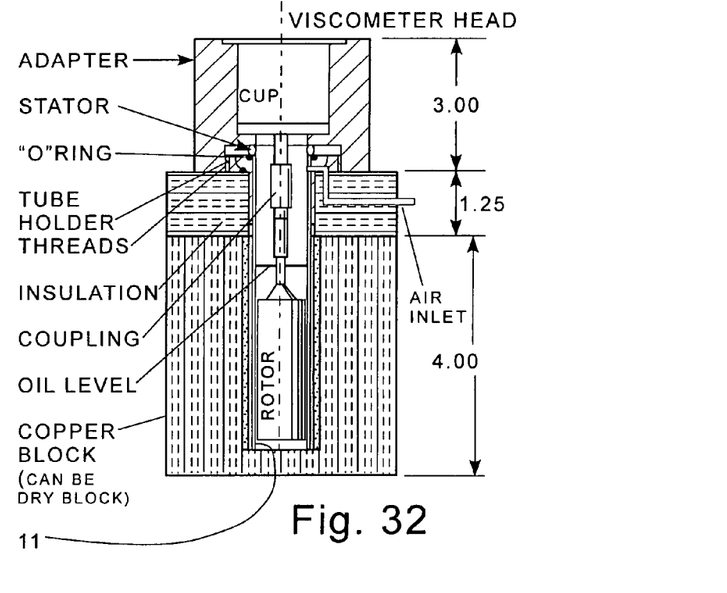
FIG. 32 is a side plan view of an SBT instrument with a rotating viscometer test station.
Figure 33:
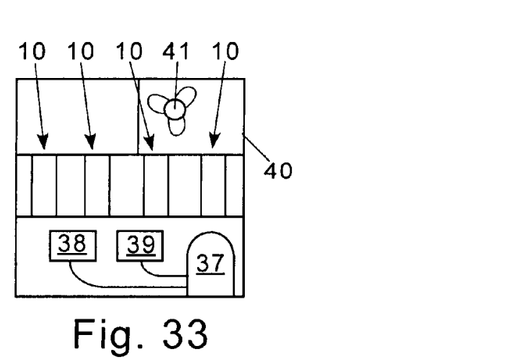
FIGS. 33-37 depict SBT rotating viscometer dry block apparatus cabinet layouts.
Figure 34:
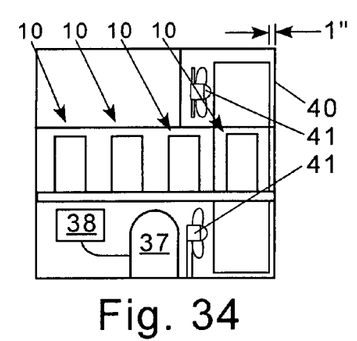
Figure 35:
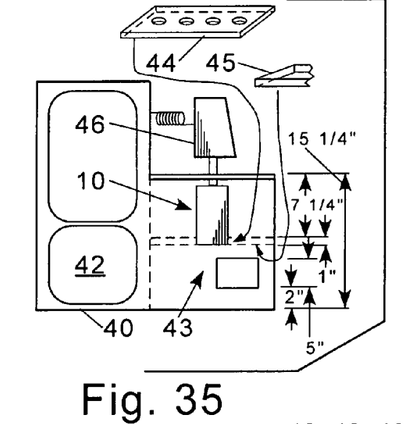
Figure 36:
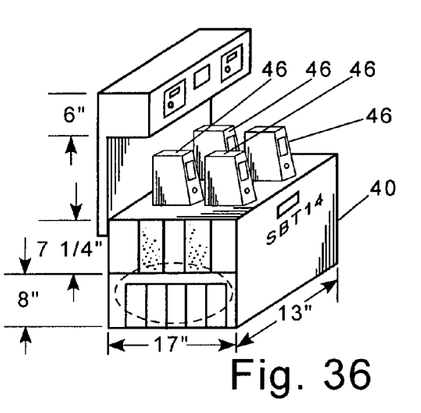
Figures 37, 39, 40:
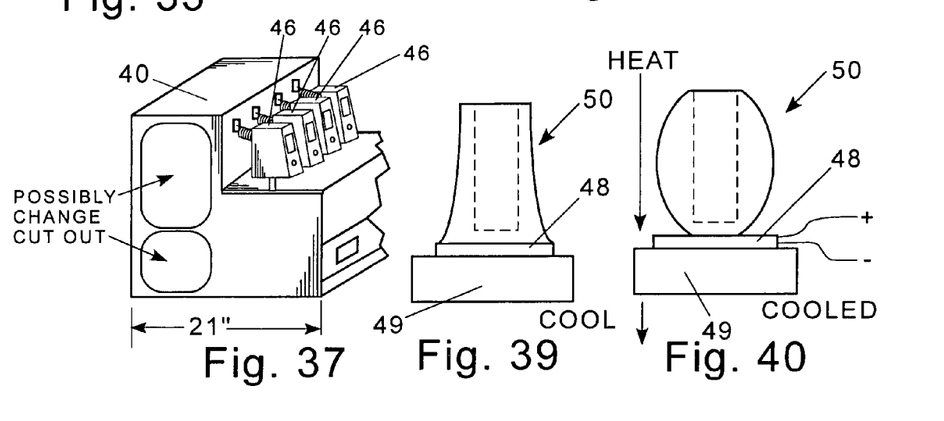
FIG. 39 is an alternative embodiment of the invention in which a thermoelectric chip is employed to provide or augment control of temperature of a test cell.
FIG. 40 is another alternative embodiment of the invention in which a thermoelectric chip is employed to provide or augment control of temperature of a test cell.
Figure 38:
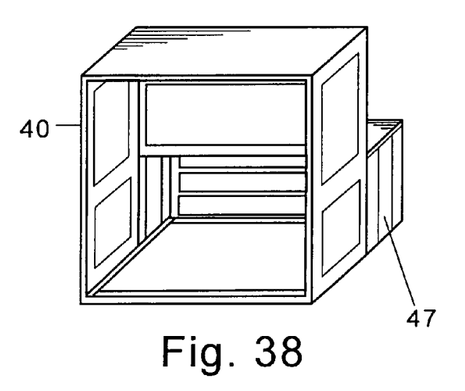
FIG. 38 is a perspective view of a cabinet that may be employed in the invention.

The foundation of the preferred scanning Brookfield dry block of the invention is its evaporator 10, which can be made of any suitable materials, to include, for example, free machining copper. Although any suitable shape for the evaporator 10 can be employed, preferably, the shape of the evaporator housing 17 and placement of its own and associated parts and features 11, 13, 14, 16, 18, 23-29 enjoy substantial if not essential symmetry about a point of axis, for instance, thus being symmetric about a central axis 9 of a rotor of an SBT viscometer with its head 46, with which the evaporator 10 is typically associated as a component part. Compare. FIGS. 1, 1B, 2-6, 11-28, 32, 35-37. In conjunction with the evaporator 10, heating by heater(s) 15, 30, for example, an electric resistance heater, which is a part of the evaporator 10, is provided. Sensor(s), which may be integral with the heater(s) 15, 30, can monitor temperature, or electrical and/or refrigerant flow through an evaporator chamber or core 13, so that computerized direction 43 and/or manual direction can be provided the heater 15, 30 and/or refrigerant flow 14, 16, 19, 20, 21, 28, 37-39, 42 to control hot and cold flux and, hence, the temperature. Compare. FIGS. 1, 1A, 1A', 31, 33-35, 37. As is well known, in a static system, where there is slow thermal response from the heat source, slow thermal transfer, and minimal change in work load, a sensor can be placed close to the heat source; in a dynamic system, where there is rapid thermal response from the heat source, rapid thermal transfer, and frequent changes in the work load, a sensor can be placed close to the work load; in a combination static-dynamic system, where the heat demand fluctuates and creates a system between static and dynamic, a sensor can be placed half-way between the heat source and work load. The evaporator 10 can be employed singly or in multiples in a block 32, say, of two, three, four, or more. Compare, FIGS. 3-10, 29, 30. When so employed, the block 32 enjoys symmetry with respect to the evaporator(s) 10. The block 32 may be insulated 33, 34. As a substitute or augmentation for the evaporator 10, electronic cooling such as by thermoelectric chip(s) 48 operating by the well known Peltier effect may be employed to cool and/or heat appropriately. Compare, FIGS. 39, 40. An adapter can be employed to join the evaporator 10 or substitute 50, with a test port sleeve 11 or test cell (stator), to an SBT viscometer head 46, which, among other things, drives a rotor and measures drag on the rotor with respect to test sample fluid in the stator, and these, the evaporator(s) 10 or substitute(s) 50 of which, again, may be mounted in the block 32, may be mounted in conjunction with a cabinet 40, also in which may be positioned a compressor, refrigerant lines 16, 19, controller(s), other electronics, and so forth. Compare, FIGS. 32-38. In any case, the test sample, for instance, an ink or an oleaginous liquid, for example, motor oil, can have its temperature controlled through the scanning of temperature for which SBT methodology is well known. With the practice of the present invention, the control of the temperature can be excellent, if not pinpoint, which is so important in the ever-demanding field of viscosity and rheology.

The following table provides further reference to the drawings (with tolerances in FIGS. 1, 3-6, 8, 9, 11, 12, 14, 15, 17, 18, 20, 21, 23, 24, 26 and 27 unless specified otherwise in which dimensions are in inches: X.XXX±0.005, X.XX±0.010, and fractions ±1/32; in which angles are ±1 degree; and in which all sharp edges are broken):

| Feature No. | Comment |
|---|---|
| 9 | Central axis |
| 10 | Evaporator |
| 11 | Removable inner sleeve (test port sleeve), for example, of #303/304 stainless steel . . . A glass test cell can be inserted therein. Use "S.I.R.T." type tool to remove for service. Inner sleeve Syntac insulation engagement, allows one plane to establish alignment. |
| 12 | Power lines, can be supplied with AC or DC voltage |
| 13 | Evaporator chamber (central core) |
| 14 | Suction line inlet located at the top, to induce refrigerant flow upwards, orifice can be at 45° |
| 15 | Ribbon heater with integral TC; thermal ribbon style resistive temperature detector (RTD); e.g., WATLOW S651; S35/S2. Control ≦0.1° C. |
| 16 | Suction line (refrigerant out), e.g., 1/4-inch copper tubing (~1/4" diameter Cu tube) . . . A small hole in the suction line located at bottom will facilitate good oil return. |
| 17 | Housing |
| 18 | Evaporator bottom |
| 19 | Capillary (cap) tube, e.g., 0.031" diameter Cu |
| 20 | Refrigerant in, cap tube entry |
| 21 | Refrigerant out, suction line exit |
| 22 | Liquid seal allows refrigerant to flash off in central core |
| 23 | Evaporator inner bottom |
| 24 | Outside evaporator sleeve |
| 25 | Material mass, use to dampen cold spot. |
| 26 | Inside evaporator sleeve |
| 27 | Air gap, between evaporator and inner sleeve, provides clearance for heaters/RTD and wires, and separates the evaporator from the inner sleeve/heater. |
| 28 | Suction line orifice, faces opposite to other one to induce rotation of refrigerant in central core |
| 29 | Evaporator top/mounting locator . . . Flange engages Syntac insulation. Entire evaporator remains a "free floating" component. |
| 30 | RTD thermal ribbon "inside" heater, next to test port sleeve . . . One or more heater(s) over RTD, one heater with integral TC for overtemperature protection |
| 31 | RTD lines |
| 32 | Block |
| 33 | Insulation, upper, e.g., Sytactic foam |
| 34 | Insulation, lower, e.g., Sytactic foam |
| 35 | Angle, should be 90° |
| 36 | Chamfer, for example, may be desired on inner sleeve to fill with brazing |
| 37 | Compressor |
| 38 | Low side manifold |
| 39 | High side manifold |
| 40 | Cabinet |
| 41 | Fan |
| 42 | Refrigeration system |
| 43 | Electronic system |
| 44 | Insulator panel |
| 45 | Pan |
| 46 | Viscometer head |
| 47 | Fuse panel |
| 48 | Cascade chip/thermoelectric chip |
| 49 | Heat sink, can be cooled. |
| 50 | Alternate evaporator . . . Use shape to determine thermal conductivity. |

As persons skilled in the art recognize, the present invention is thus clearly, concisely, exactly and fully provided. Various features, parts, subcombinations and combinations can be employed with or without reference to other features, parts, subcombinations or combinations in the practice of the invention, and numerous adaptations and modifications can be effected within its spirit, the literal claim scope of which is particularly pointed out as follows:

What is claimed is:

1. A scanning Brookfield dry block unit, which comprises a block of insulation material into which is mounted at least one component selected from the group consisting of:
   a dry block evaporator, which has a cup-like hollow housing which defines an evaporator chamber, with first and second spaced-apart bottoms, inside and outside spaced-apart walls with the first bottom connected sealingly to the inside wall and the second bottom connected sealingly to the outside wall, and a top spanning and connected sealingly to both of the inside and outside walls, into the hollow portion of which housing can enter refrigerant through a capillary and out from the evaporator chamber can exit refrigerant through suction lines; and which is for cooling a test cell placed within the inside wall and above the first bottom; and
   a cup-like housing that can be cooled and/or heated by a thermoelectric chip, which housing has a bottom and a wall, with the thermoelectric chip present and in thermal contact with the housing; and which is for cooling and/or heating a test cell placed within the wall and above the bottom;
wherein each component:
   is substantially radially symmetric with respect to a central axis for that component;
   provides temperature regulation for one and only one test cell, which is centered with respect to the central axis; and
   is substantially surrounded by insulation material of the block, at least laterally in a radial direction from the central axis; and
wherein the unit is useful for employment with or as a scanning Brookfield dry block viscometer test apparatus.

2. The unit of claim 1, which has the dry block evaporator component, two in number per unit, mounted in the same block of insulation material, wherein, in each dry block evaporator component:
   the first and second bottoms have circular outer boundaries and are oriented parallel to one another;
   the first bottom has a central protrusion with a dimple facing the second bottom;
   the inner and outer walls are cylindrical;
   the top is annular;
   the capillary enters through the second bottom, and opens toward the central protrusion with the dimple of the first bottom;
   the suction lines are two in number, and they can draw the refrigerant at positions opposite one another and spaced equally from the central axis between the inside and outside walls, and exit through the second bottom;
wherein one and only one cup-like test port sleeve is also present with each of the two dry block evaporator components, which test port sleeve has a generally cylindrical wall and a heater around its wall, and which test port sleeve is for insertion of a test cell.

3. The unit of claim 2, which contains an air gap between at least a part of the evaporator chamber and the heater.

4. The unit of claim 3, which includes at least one SBT viscometer cabinet.

5. The unit of claim 4, which further is mounted in conjunction with a cabinet.

6. The unit of claim 2, which further includes at least one SBT viscometer head.

7. The unit of claim 6, which further is mounted in conjunction with a cabinet.

8. The unit of claim 1, which further includes at least one SBT viscometer head.

9. The unit of claim 8, which further is mounted in conjunction with a cabinet.

10. The unit of claim 1, which includes the dry block evaporator component, and which further comprises:
    a test port sleeve, which sits inside the inside wall; and
    removable test port sleeve, which has associated with it a heater, and which is for insertion of a test cell;
wherein an air gap is present between at least a part of the evaporator chamber and the heater.

11. The unit of claim 10, which further includes at least one SBT viscometer head.

12. The unit of claim 11, which further is mounted in conjunction with a cabinet.

13. The unit of claim 1, which has the dry block evaporator component, and wherein:
    a cup-like test port sleeve is also present with the dry block evaporator component, which test port sleeve has a wall and a heater around its wall, and which test port sleeve is for insertion of a test cell; and
    air gap is present between at least part of the evaporator chamber and the heater.

14. The unit of claim 13, which includes at least one SBT viscometer head.

15. The unit of claim 14, which further is mounted in conjunction with a cabinet.

16. The unit of claim 1, which includes the cup-like housing that can be cooled and/or heated by the thermoelectric chip, which chip is present and in thermal contact with the housing.

17. The unit of claim 16, which includes at least one SBT viscometer head.

18. The unit of claim 17, which further is mounted in conjunction with a cabinet.

19. The unit of claim 1, which includes both components:
    the dry block evaporator; and
    the cup-like housing that can be cooled and/or heated by the thermoelectric chip, which chip is present and in thermal contact with the housing.

20. The unit of claim 1, which has mounted in the block of insulation material a plurality of the components selected from the group consisting of:
    the dry block evaporator; and
    the cup-like housing that can be cooled and/or heated by the thermoelectric chip, which chip is present and in thermal contact with the housing.

* * * * *